(12) United States Patent
Burgoyne

(10) Patent No.: US 6,322,983 B1
(45) Date of Patent: *Nov. 27, 2001

(54) SOLID MEDIUM AND METHODS FOR PROCESSING A SAMPLE OF GENETIC MATERIAL

(75) Inventor: Leigh Alexander Burgoyne, Seaford (AU)

(73) Assignee: Whatman plc, Kent (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/368,592

(22) Filed: Aug. 4, 1999

Related U.S. Application Data

(63) Continuation of application No. 08/979,978, filed on Nov. 26, 1997, now Pat. No. 5,985,327, which is a continuation of application No. 08/531,597, filed on Sep. 21, 1995, now Pat. No. 5,807,527, which is a continuation of application No. 08/159,104, filed on Nov. 30, 1993, now Pat. No. 5,496,562, which is a continuation of application No. 07/671,859, filed as application No. PCT/AU89/00430 on Oct. 3, 1989, now abandoned.

(30) Foreign Application Priority Data

Oct. 5, 1988 (AU) .................................................. 0775/88

(51) Int. Cl.[7] ................................ C12Q 1/68; A61K 9/14
(52) U.S. Cl. .............................. 435/6; 424/484; 424/486; 424/488; 424/489; 424/490
(58) Field of Search ................................... 424/486, 488, 424/489, 490, 484; 435/6

(56) References Cited

U.S. PATENT DOCUMENTS

| Re. 35,716 | 1/1998 | Stapleton et al. .................. 435/3 |
| 3,418,079 | 12/1968 | Rey et al. ........................... 23/253 |
| 3,616,259 | 10/1971 | Beutler .............................. 195/103.5 |
| 4,277,249 | 7/1981 | Broughton .......................... 23/230 B |
| 4,299,916 | 11/1981 | Litman et al. ...................... 435/6 |
| 4,455,370 | 6/1984 | Bartelsman et al. ............... 435/6 |
| 4,666,837 * | 5/1987 | Harford et al. ..................... 435/68 |
| 4,677,054 | 6/1987 | White et al. ....................... 435/6 |
| 4,695,548 * | 9/1987 | Cantor et al. ...................... 435/179 |
| 4,789,630 | 12/1988 | Bloch et al. ........................ 435/7 |
| 4,831,125 * | 5/1989 | Saltzgaber-Muller ............. 536/27 |
| 4,895,795 | 1/1990 | Frazier et al. ..................... 435/6 |
| 4,945,052 * | 7/1990 | Hardy et al. ....................... 435/172.3 |

(List continued on next page.)

FOREIGN PATENT DOCUMENTS

| 0 130 523 A2 | 1/1985 | (EP) . |
| B 30256/84 | 1/1985 | (AU) . |
| 0 221 308 A1 | 5/1987 | (EP) . |

(List continued on next page.)

OTHER PUBLICATIONS

Gibco/BRL Life Technologies catalog, 1993–1994, p. R–34.*

Bruce E. Ames, et al. "Uric Acid Provides an Antioxidant Defense in Humans Against Oxidant–and Radical–Caused Aging and Cancer: A Hypothesis," *Proc. Nat.'l Acad. Sci. USA* 79(11):6858–6862 (Nov. 1981).

Leigh Burgoyne Ph.D., et al., Safe Collection, Storage and Analysis of DNA From Blood, Abstract of Conference: 5th International Symposium on Human Identification, Oct. 8–11, 1994.

(List continued on next page.)

*Primary Examiner*—Carla J. Meyers
*Assistant Examiner*—Diana Johannsen
(74) *Attorney, Agent, or Firm*—Kohn & Associates

(57) ABSTRACT

A solid medium for storage of DNA, including blood DNA, comprising a solid matrix having a compound or composition which protects against degradation of DNA incorporated into or absorbed on the matrix. Methods for storage of DNA using this solid medium, and for recovery of DNA or in situ use of DNA are also disclosed.

4 Claims, 1 Drawing Sheet

U.S. PATENT DOCUMENTS

| | | |
|---|---|---|
| 4,965,190 | 10/1990 | Woo et al. .............................. 435/6 |
| 5,057,410 | 10/1991 | Kawasaki et al. ...................... 435/6 |
| 5,089,387 | 2/1992 | Tsay et al. .............................. 435/6 |
| 5,092,466 | 3/1992 | Anderson ............................ 206/438 |
| 5,188,963 | 2/1993 | Stapleton ............................ 435/299 |
| 5,216,132 * | 6/1993 | Basi .................................. 530/387.3 |
| 5,281,516 | 1/1994 | Stapleton et al. ....................... 435/6 |
| 5,346,672 | 9/1994 | Stapleton et al. ....................... 435/6 |
| 5,382,511 | 1/1995 | Stapleton .............................. 435/6 |
| 5,413,924 | 5/1995 | Kosak et al. ......................... 435/177 |
| 5,432,097 | 7/1995 | Yourno ................................ 436/175 |
| 5,436,129 | 7/1995 | Stapleton .............................. 435/6 |
| 5,451,500 | 9/1995 | Stapleton .............................. 435/6 |
| 5,496,562 | 3/1996 | Burgoyne ............................ 424/488 |
| 5,616,478 | 4/1997 | Chetverin et al. .................. 435/91.2 |
| 5,756,126 | 5/1998 | Burgoyne ............................ 424/488 |
| 5,807,527 | 9/1998 | Burgoyne ............................ 422/488 |
| 5,976,572 * | 11/1999 | Burgoyne ............................ 424/488 |
| 5,985,327 * | 11/1999 | Burgoyne ............................ 424/488 |

FOREIGN PATENT DOCUMENTS

| | | |
|---|---|---|
| 0 261 955 A2 | 3/1988 | (EP) . |
| WO 90/03959 | 4/1990 | (WO) . |
| WO 91/07486 | 5/1991 | (WO) . |
| WO93/07292 | 4/1993 | (WO) . |
| WO 93/19207 | 9/1993 | (WO) . |
| WO 94/26935 | 11/1994 | (WO) . |
| WO 96/11406 | 4/1996 | (WO) . |

OTHER PUBLICATIONS

Declan Butler, UK to set up DNA database of criminals . . . , *Nature* 370(6491):588–589 (Aug. 1994).

P. T. Gilham, "The Synthesis of Polynucleotide–Celluloses and Their Use in the Fractionation of Polynucleotide,:" *J. American Chem. Soc.* 86:4982–55 (Oct. –Dec. 1964).

Peter Gill, et al., "Forensic Application of DNA 'Fingerprints'", *Nature* 318:577–79 (1985).

M. Gross–Bellard, et al., "Isolation of High–Molecular–Weight DNA from Mammalian Cells," *Eur. J. Biochem.* 36: 32–38 (Jul. 2, 1973).

Michael A. Harvey, et al., "Impregnated 903 Blood Collection Paper: A Tool for DNA Preparation From Dried Blood Spots for PCR Application". (Date not available).

Innis et al., "RNA Processing: APO–B," by Lyn M. Powell, *PCR Protcols* Chapter 29, pp. 237–244 (1990).

L. Jervis et al., "Purification of Ribonuclease $T_1$ on Porous Glass Affinity Adsorbents", *J. of Chromatography* 97(1):33–38 (Oct. 1974).

Kwok–Wai Lam, et al., "Inhibition of Ascorbate Oxidation by Urate", *J. Inorganic Biochemistry*, 22(4):241–248 (1984).

Linda Madisen, et al., "DNA Banking: The Effects of Storage of Blood Isolated DNA on the Integrity of DNA", *American J. of Med. Gen.* 27(2):379–390 (1987).

T. Maniatis, et al., "Molecular Cloning—A Laboratory Manual" *Cold Spring Harbor Laboratory* Southern Transfer pp. 382–289, Preparations of Buffers and Solutions p. 447 (1982).

Stuart L. Marcus, "Purification of Avian Myeloblastosis Virus DNA Polymerase by Affinity Chromatography on Polycytidylate–Agarose", *J. of Virology* 14(4):853–859 (Oct. 1974).

Edward R.B. McCabe, et al., "DNA Microextraction from Dried Blood Spots on Filter Paper Blotters: Potential Applications to Newborn Screening", *Hum. Gent.* 75(3):213–216 (Mar. 1987).

Mohindar S. Poonian, "Covalent Attachment of Nucleic Acids to Agarose for Affinity Chromatography", *Biochemistry* 10(3):424–427 (1971).

B. Singer, et al., "Effects of Light in the Presence of Iron Salts on Ribonucleic Acid and Model Compounds" *Biochemistry* 4(2):226–233 (Feb. 1965).

Patrick E. Williams, et al., "Evaluation of a Novel Matrix for the Analysis of DNA and Its Application to Automated DNA Sample Processing", Abstract for Conference: 5th International Symposium on Human Identification, (Oct. 8–11, 1994).

Declaration of Michael J. Kvasnik (w/Exhibits A–F).

Nancy R. Webb, et al., "Purification of the Messenger RNA Cap–Binding Protein Using New Affinity Medium", *Biochemistry* 23(2):177–181 (Jan. 1984).

International Search Report and Annex to International Search Report for International Application No. PCT/AU 89/00430.

Promotional Letter from Schleicher & Schuell, dated Jul. 31, 1995.

"UltraPAK™ Customized DNA Collection Systems" brochure., 1993. (vol. #, p. 190 not applicable).

"UlstraSTAIN™ Blood Storage System" brochure, 1993. (vol. 190 , p. # not applicable).

\* cited by examiner

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TGACTGAGTA CAAACTGGTG GTG                                          23

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CTCTATGGTG GGATCATATT CA                                           22

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

TGGGCTGGAA TGGAAAGGAA TGCAAAC                                      27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO

```
        (iv) ANTI-SENSE: NO (v) FRAGMENT TYPE:

(vi) ORIGINAL SOURCE:

(xi) SEQUENCE DESCRIPTION: SEQ ID NO:4:

TCCATTCGAT TCCATTTTTT TCGAGAA                                                27

(2) INFORMATION FOR SEQ ID NO:5:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GAATGTATTA GAATGTAATG AACTTTA                                                27

(2) INFORMATION FOR SEQ ID NO:6:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

TTCCATTCCA TTCCATTCCT TTCCTTT                                                27
```

SOLID MEDIUM AND METHODS FOR PROCESSING A SAMPLE OF GENETIC MATERIAL

CROSS REFERENCE TO RELATED APPLICATIONS

The present application is a continuation application of U.S. Ser. No. 08/979,978, filed Nov. 26, 1997, now U.S. Pat. No. 5,985,327, which is a continuation of application Ser. No. 08/531,597, filed Sep. 21, 1995, now U.S. Pat. No. 5,807,527, which is a continuation of application Ser. No. 08/159,104, filed Nov. 30, 1993, now U.S. Pat. No. 5,496,562, which is a continuation of application Ser. No. 07/671,859, filed May 29, 1991, now abandoned, which is a 371 of PCT/AU89/00430, filed Oct. 3, 1989, which claims benefit of application no. PJ0775/88, filed Oct. 5, 1988.

This invention relates to a solid medium for use in the storage of DNA, particularly DNA in blood samples, and to methods which comprise the use of this solid medium. In particular, the invention relates to a method for storage and transport of DNA on the solid medium, as well as to methods which involve either (a) the recovery of the DNA from the solid medium or (b) the use of the DNA in situ on the solid medium (for example, DNA sequence amplification by the polymerase chain reaction).

BACKGROUND OF THE INVENTION

The DNA in blood samples (hereinafter referred to as "blood DNA") is used for the purposes of diagnosis of genetic diseases, diagnosis and monitoring of blood-borne parasitic diseases such as malaria, the determination of paternity, and the monitoring of other unusual cell populations in the blood as can occur in some neoplasias. For these purposes, the term "blood DNA" is used to cover all sources of DNA commonly found in blood, and thus includes the DNA of the human patient from whom the blood sample was obtained, as well as the DNA in any other organisms circulating within his/her blood.

It is a principal object of the present invention to provide a solid medium and method whereby DNA, particularly DNA in blood samples, may be conveniently and reliably stored, and if desired transported (for example from a hospital or doctor's surgery to a pathology laboratory), in a form suitable for either the recovery of the DNA for analysis or the use of the DNA in situ on the solid medium.

In the past, blood DNA has been transported as purified DNA, liquid blood, frozen blood or blood dried onto paper, however, all these methods have disadvantages. Transport of blood DNA as dried, purified DNA is most desirable, but it requires a high standard of technical assistance to be available at the places of collection. Thus, since such technical assistance is usually not available at the collection places, whole blood or other crude samples are usually sent to a central facility where the DNA is purified. Transport of liquid blood involves the need for sterility of collection and this is extremely inconvenient under some circumstances, e.g. where the sample is a heel-prick taken from an infant. The transport of liquid blood or frozen blood also demands temperature control and an appropriate transport system other than the regular postal system. This is true even before the question of hygiene is considered. In addition, the modern problems with pathogens such as the "AIDS" virus completely rule out the transport of any potentially infective liquid or frozen sample except under proper and expensive supervision.

Blood dried onto filter paper is a proven alternative to the above procedures and it has been shown that DNA can be extracted and isolated from dried whole blood spots in a form and in sufficient quantities for use in DNA analysis[1]. This procedure still suffers from a number of disadvantages. Thus, there has been no deliberate and rapid destruction of most pathogens, and there has been no deliberate inhibition of the processes degrading the DNA other than that caused by desiccation. Slow desiccation or even a small degree of rehydration under conditions of high relative humidity will allow the growth of DNA-destroying microflora. Even in the presence of bacteriostatic agents of the type that do not denature proteins, there will be conditions that permit enzymic-autolytic breakdown of the DNA and some non-enzymic breakdown of the DNA (in enzymic-autolytic breakdown, dying or damaged tissues, either human cells or parasite cells, activate enzymes that degrade their own components). There is also considerable difficulty desorbing very high molecular weight DNA from paper, if this is required. Surface adsorption effects can cause losses of DNA and this will cause the preferential loss of the least degraded, i.e. the most desired class of DNA molecules.

SUMMARY OF THE INVENTION

According to the present invention there is provided a solid medium for storage of DNA, including blood DNA, which comprises a solid matrix having a compound or composition which protects against degradation of DNA incorporated into or absorbed on the matrix.

Preferably, the solid matrix comprises a solid support, for example, an absorbent cellulose-based paper (such as filter paper) or a micromesh of synthetic plastics material, with the DNA-protecting compound or composition absorbed onto the solid support. Alternatively, the solid matrix may include a suitable binder material so that the matrix is in the form of a compressed tablet or pellet, with the DNA-protecting compound or composition incorporated into or absorbed onto the tablet or pellet.

DETAILED DESCRIPTION OF THE INVENTION

Figure 1:
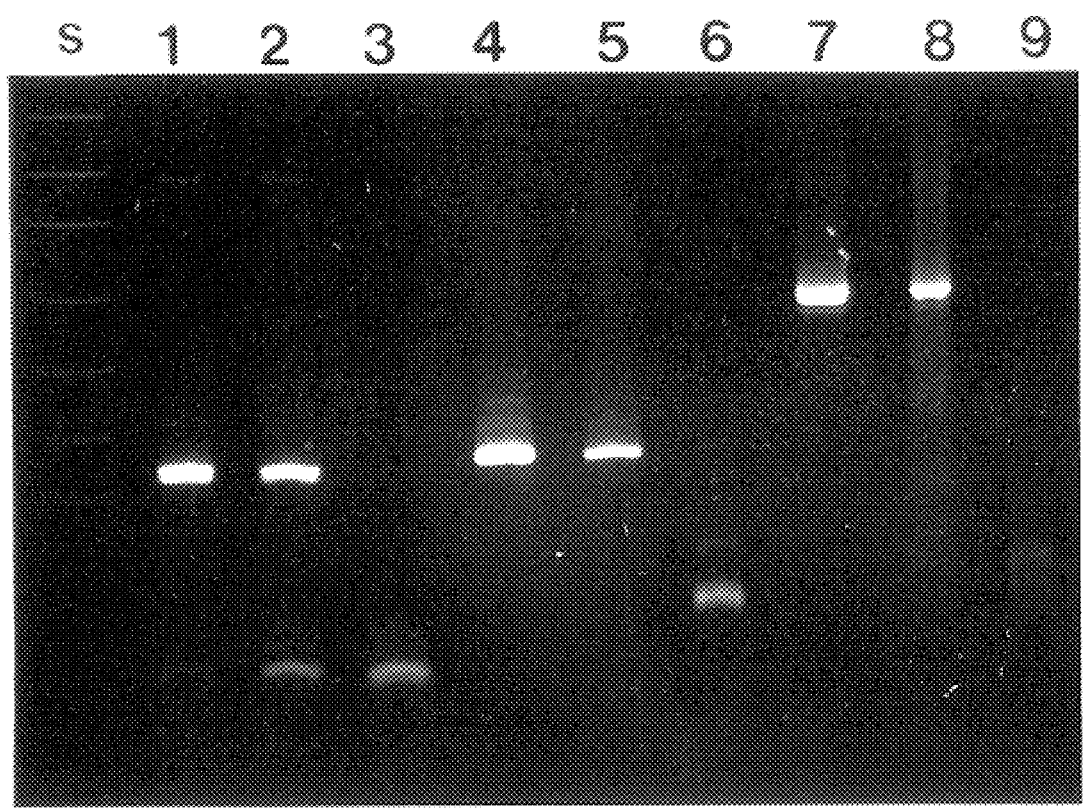
FIG. 1: An analysis of products from PCR of extracted DNA and treated DNA filter papers, as follows: Lanes 1–3: target No. 1, lane 1: 1 $\mu$g DNA, lane 2: 1 $mm^2$ filter, lane 3: no DNA control; lanes 4–6: target no. 2, lane 4: 1 $\mu$g DNA, lane 5: 1 $mm^2$ filter, lane 6: no DNA control; lanes 7–9: target no. 3, lane 7: 1 $\mu$g DNA, lane 8: 1 $mm^2$ filter, lane 9: no DNA control; lane S: DNA size markers (pUC19/HpaII digest).

In its broadest aspect, the present invention also provides a method for the storage of DNA, including blood DNA, which comprises applying the DNA to a solid medium which comprises a solid matrix having a compound or composition which protects against degradation of DNA incorporated into or adsorbed on the matrix.

In one embodiment of the invention, particularly for long term storage of purified DNA, the DNA-protecting compound or composition comprises uric acid, together with a weak base to convert the uric acid to a urate salt and to provide an alkaline pH between 8.0 and 9.5.

In one particularly preferred aspect of the present invention, there is provided a solid medium for storage of blood DNA, which comprises a solid matrix having incorporated therein or absorbed thereon a composition comprising a weak base, a chelating agent and an anionic surfactant or detergent, and optionally uric acid or a urate salt.

Preferably, the composition imposes an alkaline pH, such as a pH of between 8.0 and 9.5, on blood that is added to the matrix.

A further aspect of the present invention is the long term storage of DNA on the solid medium of this invention, by impregnating the solid medium or encasing the solid medium in a protective material, for example a plastics material such as polystyrene, which can be subsequently removed when access to the stored DNA is required.

In practice, in the storage of Blood DNA the blood sample is applied as a blood spot to the solid medium of this aspect of the invention, where the components more particularly the surfactant will denature proteins and the majority of any pathogenic organisms in the sample. At the same time, however, the blood DNA will be protected from degradation factors and processes of the type described above so that the relatively stable, and denatured, dried blood sample can then be transported to a diagnostic laboratory. There, the DNA can be extracted or the DNA used in situ on the solid medium.

Preferably, the composition used in this aspect of this invention comprises the following:
(i) a monovalent weak base (such as "Tris", tris-hydroxymethyl methane, either as the free base or as the carbonate);
(ii) a chelating agent (such as EDTA, ethylene diamine tetracetic acid); and
(iii) an anionic detergent (such as SDS, sodium dodecyl sulphate); and optionally
(iv) uric acid or a urate salt.

By way of example, a particularly preferred solid medium according to this aspect of the invention comprises an absorbent cellulose-based paper such as filter paper having a minimal loading, per sq.cm. of paper, as follows:
(a) EDTA: 0.5 micromols (146.1 mg of free acid)
(b) Tris: 8 micromols (968.8 mg of free base)
(c) SDS: 1 mg; and optionally
(d) uric acid: 2 micromols (336.24 mg of acid).

Although not vital for the short-term storage of DNA on the solid medium, the use of uric acid or a urate salt in accordance with this invention has been found to be particularly important for the long term storage of DNA as this component performs a number of functions. Firstly, it is converted into allantoin in acting as a "free-radical" trap that preferentially accepts free radicals, that would otherwise damage the base guanine in the DNA, (e.g. [2,3]). Such free radicals are generated by the spontaneous oxidation of thio groups in the denatured serum protein, and may also be generated by the large amount of iron in blood[4]. The uric acid also acts as a component of the buffering system in that it is a weak acid. It also acts as an erodible surface in that it is sparingly soluble so that DNA-containing material dried onto its crystals will be released as the urate beneath them erodes.

As previously described, the composition may include a base, optionally a monovalent weak base, to cause an alkaline pH between 8.0 and 9.5 to be imposed upon the blood that is placed upon the matrix. This is to ensure the proper action of the chelating agent in binding divalent metals. It is also to prevent the action of acid nucleases that are not so dependent on divalent metals. The base may be a weak organic base, such as Tris. Alternatively, an inorganic base such as an alkali metal carbonate or bicarbonate, for example sodium, lithium or potassium carbonate or bicarbonate, may be used.

The chelating agent is preferably a strong chelating agent such as EDTA, however a wide range of suitable strong chelating agents are commercially available. The function of the chelating agent is to bind the divalent metal ions, magnesium and calcium, and also to bind transition metal ions, particularly iron. Both calcium and magnesium are known to promote DNA degradation by acting as co-factors for enzymes. The metal ions such as iron, that readily undergo oxidation and reduction also damage nucleic acids by the production of free radicals[4].

The anionic surfactant or detergent is included in the composition of this aspect of the invention as the primary denaturing agent. Any strong anionic detergent that binds to and denatures proteins is suitable, and as well as SDS mentioned above other detergents such as sodium lauryl sarcosinate may also be used. This anionic detergent causes most pathogens to be inactivated due to the non-specific destruction of the secondary structure of their coat proteins, their internal proteins, and any membranes they may be dependent upon. There are exceptions, since the anionic detergent does not inactivate the most resistant bacterial spores, nor does it inactivate some extremely stable enteric virions. However, these exceptions are agents that are already likely to be transferred by ordinary contact and there is currently no great concern that these agents constitute a risk from blood.

In tests leading to the present invention, it has been demonstrated that blood DNA can be extracted satisfactorily from detergent-treated paper and that uric acid salt protects purified DNA against degradation during storage for more than 36 months. In further tests, DNA on filter paper specially treated in accordance with this invention was purified in situ, then subjected to the polymerase chain reaction (PCR). Details of these tests are set out in the following Examples.

EXAMPLE 1

Collection and Extraction of DNA

Sodium dodecyl sulphate was applied to Whatman 3 mm paper in a solution such that there was approximately 50 $\mu$l per sq.cm. of a solution of 2% sodium dodecyl sulphate, 10 mM EDTA, and 60 mM tris (free base), i.e. approximately 1 mg of sodium dodecyl sulphate per sq.cm. The paper was then dried.

The treated paper was soaked with drops of blood from various primates. The blood-stained paper was dried, sent through the ordinary mail so that it spent at least three days in the mail, and then had the DNA extracted from it using standard procedures involving detergent-aided proteolysis and phenol extraction of the paper. The resultant DNA was then tested for its quality by being digested with restriction endonucleases and the fragments analyzed by agarose gel electrophoresis.

The DNA fragments were found to be as high in quality as DNA produced from fresh blood. This demonstrates that the DNA can be extracted from detergent-treated papers and that the DNA is of sufficient quality for most normal purposes.

EXAMPLE 2

Long-term Storage of Semi-purified or Purified DNA

Storage of DNA, such as plasmids or other viral replicating forms, has been carried out using record cards made of absorbent paper previously soaked in a solution of uric acid and tris (free base). The cards are subsequently plasticised for further protection. This procedure has been established for the long-term storage of clones from massed dot-blots when it is possible that the original material is required at some much later date, and when a great many such massed clonings are to be kept in orderly, low-volume, files. Samples have been stored successfully this way for about four years.

2.1 Preparation of DNA Record Cards

Record cards can be prepared in batches and stored until needed. Whatman No.1 paper about 10 cm×15 cm in size and with appropriate places marked out with an "indian ink" (i.e. colloidal carbon ink-stamp) is suitable, and any special notes on the cards can be made with an ordinary "lead" pencil (i.e. Graphite pencil). Preferably, the cards are marked out in a regular pattern to assist in systematic storage and retrieval of DNA samples.

Marked cards are wrapped in clean paper, then foil, and autoclaved with a dry cycle. They are then treated with a solution of 40 mM uric acid and 100 mm tris (free base). The function of the urate is to protect the DNA from aging and to aid the desorption from the paper if required. These treated record cards can then be kept until required.

2.2 DNA Samples and Their Application

DNA to be stored is taken up in a dilute alkaline buffer containing EDTA, e.g. TE buffer (Tris-EDTA pH 8.0). By way of example, approx 1 ml of bacterial culture containing plasmid, is treated by the alkaline lysis method, with one phenol extraction and one alcohol precipitation, to get approx 50 $\mu$l of plasmid or other DNA in TE buffer. A 5 $\mu$l aliquot of each DNA sample is used to make a spot on the urate treated record card.

2.3 Impregnation of DNA-loaded Cards with Plastic

Once a card is fully loaded with DNA samples, the DNA spots are thoroughly air-dried, then the card is dipped in 5 ml of 12% w/v polystyrene in acid-free chloroform. This is preferably achieved by putting the card in a fitting polyethylene baglet and then pouring the polystyrene solution into it, spreading the polystyrene solution to thoroughly coat the card and then stripping off the soiled polyethylene. The card is then allowed to dry at room temperature.

2.4 Storage Conditions

The cards are conveniently stored in a sealed container in a refrigerator freezer (about −15° C.) in the presence of drying agent such as silica gel and a few grains of dry sodium carbonate to remove any traces of acid vapours.

2.5 Using DNA on Plasticised Cards

The storage container is allowed to rise to room temperature in order to minimise unnecessary wetting and drying cycles on long-term storage cards. The appropriate card is abstracted, the relevant DNA spot identified and a small sample of it cut out.

Since the 5 $\mu$l spots are laid out in a regular fashion, it is quite practical to cut them across with a scalpel blade to remove a portion of the sample, e.g. one-quarter of a spot. This is then placed in a disposable plastic tube with approximately 5 ml of acid-free chloroform, capped and rotated on a blood rotator at room temperature for at least 30 minutes. This removes the protective polystyrene and effectively sterilises the sample also. DNA may then be eluted from the sample or the sample can be treated and used in situ, for example in a DNA sequence amplification reaction (PCR) (see later).

In an example, the desorption of DNA samples, both single and double stranded, from Whatman No.1 paper soaked with a solution of 40 mM uric acid, and 100 mM tris (free base) was examined by using the plasmid pUC19 as a source of standard double stranded DNA and M13 as a source of single stranded DNA.

In both cases, samples of the DNA were dried onto paper from solutions in TE buffer and the paper was then sheathed in protective polystyrene, as described above. The paper was later chloroform extracted to remove the protective layers, the DNA extracted with fresh TE buffer and the efficiency of extraction estimated by observing the transformation of the *E. coli* strain JM101 by the extracted DNA. This procedure was carried out with both untreated paper and paper that had been pre-soaked and dried with the above urate solution. Much less than 10% of transformationally active DNA was successfully recovered from the untreated paper, whereas the treated paper gave recoveries of approximately 100%.

Further DNA samples which had been applied to treated paper and sheathed as previously described, were tested after 36 months storage in a dry atmosphere at −15° C. The samples again had the plastic stripped off with chloroform, the DNA (only pUC19) recovered by simple extraction with TE buffer, and the DNA activity tested as previously described. Again the activity of the DNA was high, compatible with virtually no loss of activity.

EXAMPLE 3

In situ Use of Stored Blood DNA in PCR

Blood DNA stored on filter paper treated in accordance with the present invention can be amplified in situ by the polymerase chain reaction (PCR) technique. The treated paper used in this Example was Whatman 3 mm paper treated with a solution comprising, per sq.cm. of paper, 2 micromols uric acid, 8 micromols tris (free base), 0.5 micromols EDTA and 1 mg SDS. The stored blood DNA was treated to remove protein, then washed to remove phenol and add suitable ions, prior to DNA amplification.

3.1 Solutions

Solution A:
    One-phase Phenol solution. A suitable mixture is phenol, 50 gm containing 120 mg of 8-hydroxyquinoline that has been saturated with 10 ml of 1.0 M tris-acetate pH 8.0 and 1.0 ml 2-mercaptoethanol. After saturation by shaking at room temperature, the aqueous phase is thoroughly removed and discarded.
Solution B:
    75% v/v Isopropanol, 25% v/v 0.1 M potassium acetate at pH 7.8.
Solution C:
    75% v/v Isopropanol, 25% v/v 0.01 M magnesium acetate.
(Note that other alcohols or similar water-miscible solvents, e.g. n-propanol, may be substituted for isopropanol in these solutions.)

3.2 Method

All steps are preferably carried out in a single tube made of a suitable phenol resistant material, e.g. polyethylene.
(a) Removal of Protein: a 0.5 cm×0.5 cm square of blood DNA impregnated paper is treated with 1 ml of solution A, for example for approximately 1.5 hours at 45° C. (this temperature and time is not critical). The dirty solution A is then aspirated to waste and the paper square quickly washed three times with 0.25 ml of more solution A. Each wash need be only a few seconds long and is immediately aspirated to waste.

(b) Removal of phenol and addition of suitable ions: the paper in its tube from step (a) above, is rapidly washed in three lots of 1 ml of solution B. Washes are at room temperature and are simple additions followed by aspiration to waste. The paper is then washed for 20 minutes at room temperature with solution C. (This is to saturate the DNA on the paper with Magnesium ions and remove the last of the phenol.) The solution C is aspirated to waste and the paper is solvent-dried with one wash of pure isopropanol and then vacuum dried.

The final DNA-paper should be quite white without any obvious remnants of the red-brown colour of blood. It is now ready for use in a PCR reaction mix.

(c) Amplification of DNA on treated paper: The treated DNA-paper as described above has been shown to be a suitable substrate for DNA polymerase chain reaction (PCR) amplification of DNA.

(i) Specimens

Extracted DNA: DNA from 10 ml of blood obtained from a male volunteer was extracted by standard protocols.

Treated DNA Filter Paper: Blood specimens from the same volunteer were applied directly to treated filter paper with subsequent treatment as described above. The paper was cut into about 1 mm$^2$ pieces for use in PCR reactions.

(ii) Targets for Amplification.

Target No. 1: Region of exon 2 of the n-Ras proto-oncogene on chromosome 1. The primers used are:

R1: 5' TGA CTG AGT ACA AAC TGG TGG TG 3' (SEQ ID NO:1) and

R2: 5' CTC TAT GGT GGG ATC ATA TTC A 3' (SEQ ID NO:2).

The amplified DNA fragment obtained with these primers is 110 bp in size.

Target No.2: A male specific Y chromosome repeat sequence. The primers are:

007: 5' TGG GCT GGA ATG GAA AGG AAT GCA AAC 3' (SEQ ID NO:3) and

008: 5' TCC ATT CGA TTC CAT TTT TTT CGA GAA 3' (SEQ ID NO:4).

The amplified DNA fragment obtained with these primers is 124 bp in size.

Target No.3: A male specific Y chromosome repeat sequence. The primers used are:

004: 5' GAA TGT ATT AGA ATG TAA TGA ACT TTA 3' (SEQ ID NO:5) and

006: 6' TTC CAT TCC ATT CCA TTC CTT TCC TTT 3' (SEQ ID NO:6).

The amplified DNA fragment obtained with these primers is 250 bp in size.

(iii) PCR Protocol

Extracted DNA (1 μg) or about 1 mm$^2$ fragments of treated DNA filter paper were placed into 0.5 ml Eppendorf tubes and made to 25 μl in PCR reaction mixture consisting of:

67 mM Tris HCl (pH 8.8 @ 25° C.)
16.6 mM ammonium sulfate
2 mM MgCl$_2$
0.01% (w/v) gelatin
0.1 mM deoxynucleotides (dATP, dTTP, dCTP, dGTP)
0.25 μg of each primer (for respective target)
0.25 U of Taq DNA polymerase.

The mixture was overlaid with 25 μl of light mineral oil and DNA application was performed by 30 cycles of amplification on a Perkin Elmer-Cetus "thermal cycler".

The first cycle consisted of:

| | |
|---|---|
| DNA denaturation | 6 min. @ 94° C. |
| Primer-DNA annealing | 1 min. @ 55° C. |
| Taq DNA polymerase extension | 1 min. @ 75° C. | followed by 29 cycles as above except DNA denaturation was for 1 min @ 94° C. and the extension time on the last cycle was 10 min @ 72° C. before cooling of reaction mixture to 4° C.

After amplification, 10 μl aliquots of PCR mixture were analysed by electrophoresis on 15% (w/v) polyacrylamide gels. Amplified target DNA was visualized by UV illumination of the ethidium bromide stained gel. An analysis of products from PCR of extracted DNA and treated DNA filter papers as shown in FIG. 1, as follows: Lanes 1–3: target No.1, lane 1: 1 μg DNA, lane 2: 1 mm$^2$ filter, lane 3: no DNA control; Lanes 4–5: target No.2, lane 4: 1 μg DNA, lane 5: 1 mm$^2$ filter; Lane 6: no DNA control; Lanes 7–9: target No.3, lane 7: 1 μg DNA, lane 8: 1 mm$^2$ filter, lane 9: no DNA control; lane S: DNA size markers (pUC19/HpaII digest).

The results shown clearly demonstrate that the DNA has not been changed in any way as a result of its storage on filter paper in accordance with this invention, and that it can be used in situ as described herein.

It will be readily apparent to those skilled in the art that the above solid-state steps for purification and amplification of blood DNA are particularly suited for performance under automated conditions.

REFERENCES

1. McCabe, E. R. B., Huang, S. Z., Seltzer, W. K. and Law, M. L. (1987). *Hum. Genet.* 75: 213–216.
2. Ames, et.al. (1981). *Proc. Natl. Acad. Sci.(USA).* 78: 6858–6862.
3. Kwok Lai Lam, Fong, D., Lee, A. and Ken Ming D. Lui. (1984), *J. Inorg. Biochem.* 22: 241–248.
4. Singer, B. and Fraenkel-Conrat, H. (1965). *Biochemistry* 4: 226–223.

What is claimed is:

1. A solid medium for processing a sample of genetic material, the solid medium consisting of:
   (a) a solid matrix; and
   (b) a composition which protects against degradation of genetic material applied to the solid matrix, the composition consisting of:
      (i) a protein denaturing agent; and
      (ii) an inhibitor of an action of a nuclease.

2. A method for processing a sample of genetic material, the method consisting essentially of:
   (a) applying a sample of genetic material to a solid medium wherein the solid medium consists of:
      (i) a solid matrix; and
      (ii) a composition which protects against degradation of genetic material, the composition being adsorbed or incorporated onto the solid matrix, the composition consisting of a protein denaturing agent and an inhibitor of an action of a nuclease; and
   (b) processing the sample of genetic material applied to the solid medium.

3. A method for processing a sample of genetic material, the method consisting essentially of:
   (a) applying a sample of genetic material to a solid medium wherein the solid medium comprises:
      (i) a solid matrix; and
      (ii) a composition which protects against degradation of genetic material, the composition being adsorbed or incorporated onto the solid matrix, the composition comprising a protein denaturing agent, a chelating agent, and uric acid; and
   (b) processing the sample of genetic material applied to the solid medium.

4. A solid medium for storing a sample of genetic material, the solid medium consisting of:
   (a) a solid matrix; and
   (b) a composition which protects against degradation of genetic material adsorbed or incorporated onto the solid matrix, the composition consisting of:
   (i) a protein denaturing agent;
   (ii) a compound that binds ions which promote degradation of DNA; and
   (iii) a buffer.

* * * * *